(12) United States Patent
Dibas et al.

(10) Patent No.: US 8,501,796 B2
(45) Date of Patent: *Aug. 6, 2013

(54) ESTER PRO-DRUGS OF [3-(1-(1H-IMIDAZOL-4-YL)ETHYL)-2-METHYLPHENYL] METHANOL FOR LOWERING INTRAOCULAR PRESSURE

(75) Inventors: Mohammad I. Dibas, Laguna Niguel, CA (US); Daniel W. Gil, Corona Del Mar, CA (US); John E. Donello, Dana Point, CA (US); Ken Chow, Newport Coast, CA (US); Liming Wang, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/233,844

(22) Filed: Sep. 15, 2011

(65) Prior Publication Data

US 2012/0142746 A1    Jun. 7, 2012

Related U.S. Application Data

(60) Provisional application No. 61/383,370, filed on Sep. 16, 2010.

(51) Int. Cl.
 *A61K 31/415*    (2006.01)
(52) U.S. Cl.
 USPC .......................................... 514/396; 514/385
(58) Field of Classification Search
 USPC ................................................. 514/396, 385
 See application file for complete search history.

(56) References Cited

U.S. PATENT DOCUMENTS

| 5,474,979 | A | 12/1995 | Ding |
| 6,582,718 | B2 | 6/2003 | Kawashima |
| 7,297,679 | B2 | 11/2007 | Chang |
| 7,491,383 | B2 | 2/2009 | Woodward |
| 2004/0214829 | A1* | 10/2004 | Graham et al. ............... 514/249 |
| 2005/0059583 | A1 | 3/2005 | Acheampong |
| 2005/0277584 | A1 | 12/2005 | Tien |
| 2007/0015691 | A1 | 1/2007 | Chang |
| 2011/0301214 | A1* | 12/2011 | Gil .............................. 514/400 |

FOREIGN PATENT DOCUMENTS

| WO | WO 95-14007 | 5/1995 |
| WO | WO 2005-034998 | 4/2005 |
| WO | WO 2006-036480 | 4/2006 |
| WO | WO 2009-089132 | 7/2009 |
| WO | WO 2010-091209 | 8/2010 |
| WO | WO 2010-093930 | 8/2010 |

OTHER PUBLICATIONS

Winfield, Pharmaceutical Practice, Ophthalmic Products-Formulation of Eye Drops,Churchill Livingstone, 2004, 264-271.*

(Continued)

*Primary Examiner* — Gigi Huang
(74) *Attorney, Agent, or Firm* — Doina G. Ene

(57) ABSTRACT

The present invention relates to method of lowering intraocular pressure in a subject in need of such treatment, which comprises administering a therapeutically effective amount of a composition comprising a ester pro-drugs of [3-(1-(1H-imidazol-4-yl)ethyl)-2-methylphenyl]methanol, of enantiomers thereof, of tautomers thereof, pharmaceutical compositions containing them and their use as pharmaceuticals.

18 Claims, 1 Drawing Sheet

OTHER PUBLICATIONS

Stoilov et al., Synthesis of detomidine and medetomidine metabolites: 1,2,3-trisubstituted arenes with 4'(5')-imidazolylmethyl groups, Journal of Heterocyclic Chemistry (1993), 30(6), 1645-1651.*
Vippagunta et al., Crystalline solids, 2001, Advanced:Drug Delivery Reviews, 48, 3-26.*
Braga et al., Chem. Commun., "Making Crystals from Crystals: a green route to crystal engineering and polymorphism," 2005, pp. 3635-3645.*
Seddon, K.R., "Pseudopolymorph: a polemic," Crystal Growth & Design, 2004, 4(6), pp. 1087, web release date Oct. 19, 2004.*
Gentili, Francesco et al., "Agonists and Antagonists Targeting the Different Alpha(2)-Adrenoceptor Subtypes," Current Topics in Medicinal Chemistry, vol. 7, No. 163-186, Jan. 1, 2007.
Lee, Vincent et al., "Prodrugs For Improved Ocular Drug Delivery," Advanced Drug Delivery Reviews, vol. 3, No. 1, 1-38, Jan. 1, 1989.
Jaanus, Siret et al, "Antiinflammatory Drugs," Clinical Ocular Pharmacology, Bartlet, J.D. and Jaanus, S.D., Ed., Boston: Heineman, pp. 265-298, 2001.
Noecker, Robert, "Ophthalmic preservatives: Considerations for long-term use in patients with dry eye or glaucoma," Review of Ophthalmology, Jun. 2001.
Stella, V. et al., "Pro-drugs as Novel Delivery System", vol. 14 of the A.C.S. Symposium Series "Bioreversible Carriers in Drug Design", ed. Edward B. Roche, American Pharmaceutical Association and Pergamon Press, 1987.
Patent Cooperation Treaty, Notification of Transmittal of the International Search Report and the Written Opinion of the International Searching Authority, or the Declaration, Form PCT/ISA/220, Int. App. No. PCT/US2011/051990, Oct. 31, 2011.
Stahl, Heinrich & Wermuth, Camille (Eds), Handbook of Pharmaceutical Salts, Verlag Helvetica Chemica Acta-Zürich, 329-345, 2002.
Testa, Bernard et al., "Design of Intramolecularly Activated Prodrugs," Drug Metabolism Reviews, vol. 30, No. 4, 787-807, Jan. 1, 1998.

* cited by examiner

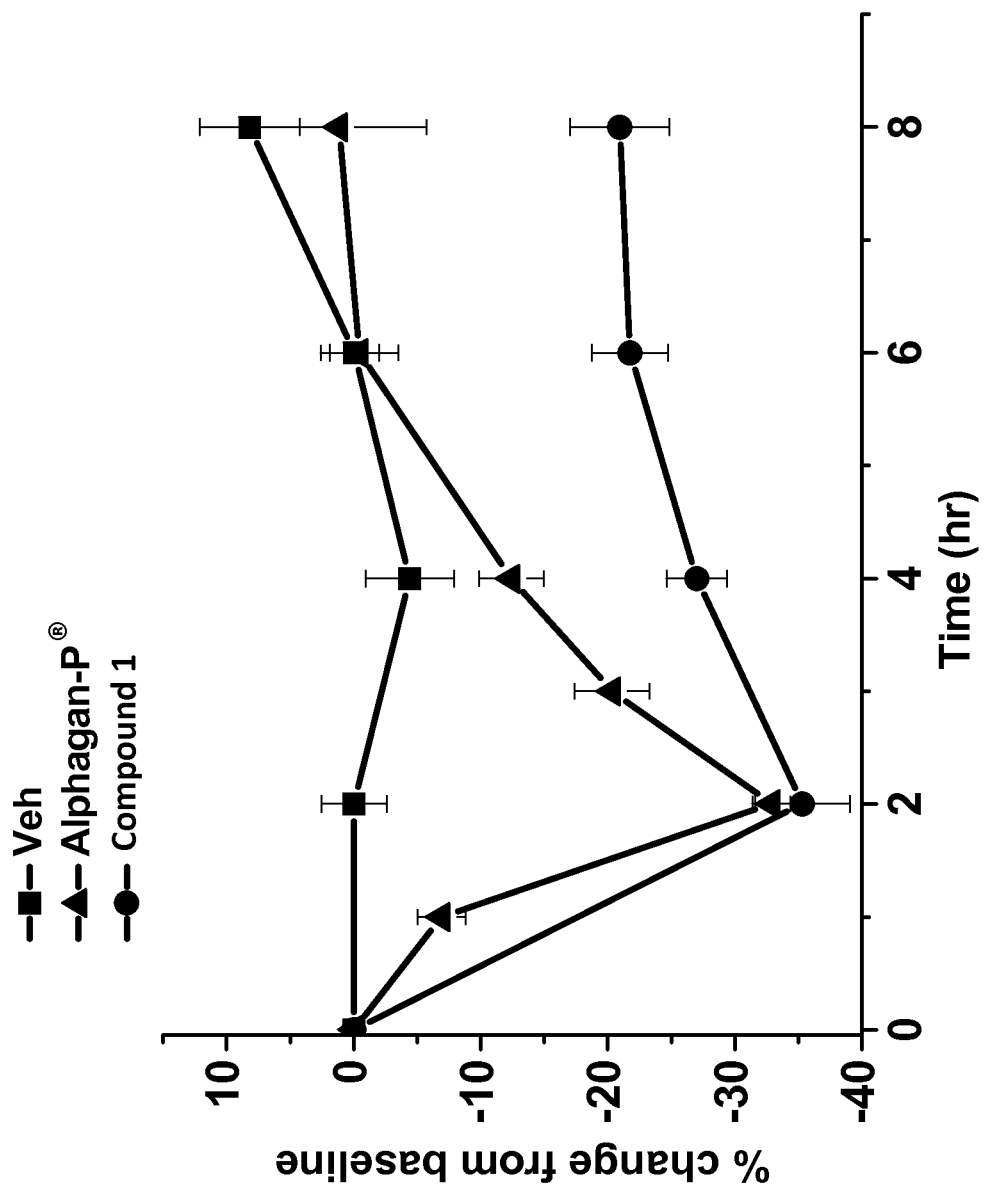

ESTER PRO-DRUGS OF [3-(1-(1H-IMIDAZOL-4-YL)ETHYL)-2-METHYLPHENYL] METHANOL FOR LOWERING INTRAOCULAR PRESSURE

RELATED APPLICATIONS

This application claims priority to U.S. Provisional Patent Application No. 61/383,370 filed on Sep. 16, 2010, the entire disclosure of which is incorporated herein by this reference.

BACKGROUND OF THE INVENTION

1. Field of the Invention

The present invention relates to a method of lowering intraocular pressure in a subject in need of such treatment, which comprises administering a therapeutically effective amount of a composition comprising ester pro-drugs of [3-(1-(1H-imidazol-4-yl)ethyl)-2-methylphenyl]methanolor of its enantiomers.

2. Summary of the Related Art

Three alpha-1 and three alpha-2 adrenergic receptors have been characterized by molecular and pharmacological methods. Activation of these alpha receptors evokes physiological responses with useful therapeutic applications.

Compound, 4-[1-(2,3-dimethylphenyl)ethyl]-3H-imidazole, generically known as, medetomidine is an alpha 2 adrenergic agonist, for use in the sedation of animals. The hydrochloride salt of the (S) enantiomer of medetomidine, generically known as dexmedetomidine, (S) 4-[1-(2,3-dimethylphenyl)ethyl]-3H-imidazole, is also indicated for use as a sedative or analgesic in cats and dogs.

The metabolite of dexmedetomidine is (S) [3-(1-(1H-imidazol-4-yl)ethyl)-2-methylphenyl]methanol together with its racemic mixture, compound [3-(1-(1H-imidazol-4-yl)ethyl)-2-methylphenyl]methanol, are described in the literature in *Journal of Chromatography*, (1997), 762(1+2), 281-291 by Hui, Y.-H et al. [3-(1-(1H-imidazol-4-yl)ethyl)-2-methylphenyl]methanol is described in "Synthesis of detomidine and medetomidine metabolites: 1,2,3-trisubstituted arenes with 4'(5')-imidazolylmethyl groups" in *Journal of Heterocyclic Chemistry* (1993), 30(6), (1645-1651) by Stoilov et al.

Kavanagh, et al. describe [3-(1-(1H-imidazol-4-yl)ethyl)-2-methylphenyl]methanol in "Synthesis of Possible Metabolites of Medetomidine {1-(2,3-dimethylphenyl)-1-[imidazol-4(5)-yl]ethane" in *Journal of Chemical Research, Synopses* (1993), (4), 152-3.

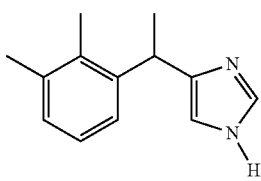

Medetomidine
4-(1-(2,3-dimethylphenyl)ethyl)-1H-imidazole
CAS 86347-14-0

-continued

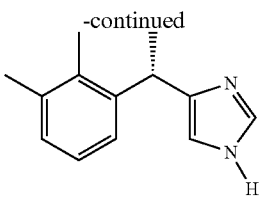

Dexmedetomidine
(S)-4-(1-(2,3-dimethylphenyl)ethyl)-1H-imidazole
CAS 189255-79-6

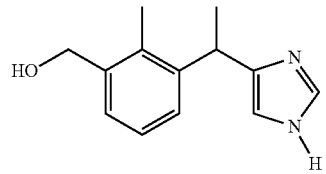

(3-(1-(1H-imidazol-4-yl)ethyl)-2-methylphenyl)methanol
CAS 128366-50-7

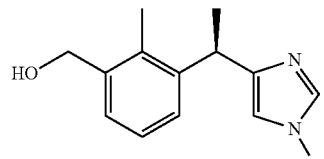

(R)-(3-(1-(1H-imidazol-4-yl)ethyl)-2-methylphenyl)methanol
CAS 1240244-32-9

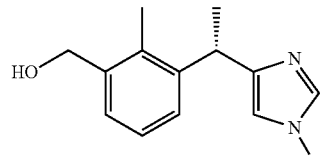

(S)-(3-(1-(1H-imidazol-4-yl)ethyl)-2-methylphenyl)methanol
CAS 189255-79-6

[3-(1-(1H-imidazol-4-yl)ethyl)-2-methylphenyl)methanol] is described by Salonen, et al. in "Biotransformation of Medetomidine in the Rat" in *Xenobiotica* (1990), 20(5), 471-80.

PCT Int. Appl. WO 2010093930 A1 discloses [3-(1-(1H-imidazol-4-yl)ethyl)-2-methylphenyl]methanol and its (S) and (R) enantiomers

SUMMARY OF THE INVENTION

Three alpha 1 and three alpha 2 adrenergic receptors have been characterized by molecular and pharmacological methods. Activation of these alpha 2 receptors evokes physiological responses and has useful therapeutic actions.

The adrenergic Alpha-2 agonists play a key role in modulating aqueous humor formation and facilitating aqueous outflow; as a result these compounds lower intraocular pressure (IOP) in glaucomatous patients. Two drugs are currently prescribed for glaucoma patients, Apraclonidine (Iopidine® available from Alcon Pharmaceuticals) and Brimonidine (Alphagan P® available from Allergan, Inc.). While these drugs are effective at lowering elevated intraocular pressure, Alphagan P® is the only alpha-2 adrenergic drug approved for chronic treatment of glaucoma, but it loses effect during the day and must be used 2-3 times a day, while Iopidine® is only approved for short term IOP control. Considering the aged glaucoma patient population, a 3 times per day dosing frequency is far from optimal and may result in poor patient compliance.

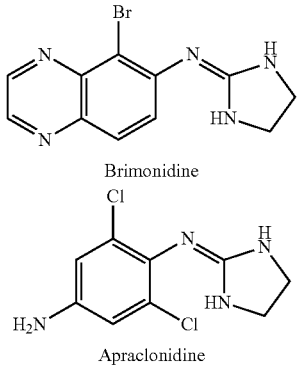

Brimonidine

Apraclonidine

The present invention relates to a method of lowering intraocular pressure in a subject in need of such treatment, which comprises administering a therapeutically effective amount of a composition comprising ester pro-drugs of [3-(1-(1H-imidazol-4-yl)ethyl)-2-methylphenyl]methanol. Upon hydrolytic and/or enzymatic cleavage of the ester functionality the parent compound, [3-(1-(1H-imidazol-4-yl)ethyl)-2-methylphenyl]methanol, is released to act as a selective modulator of the alpha 2 adrenergic receptors.

In another aspect, the present invention relates to a method of lowering intraocular pressure in a subject in need of such treatment, which comprises administering a therapeutically effective amount of a composition comprising ester pro-drugs of (S) [3-(1-(1H-imidazol-4-yl)ethyl)-2-methylphenyl]methanol, or pharmaceutical compositions containing them. Upon hydrolytic and/or enzymatic cleavage of the ester functionality the parent compound, active metabolite, (S) [3-(1-(1H-imidazol-4-yl)ethyl)-2-methylphenyl]methanol, is released to act as a selective modulator of the alpha 2 adrenergic receptors.

In another aspect the present invention provides relates to a method of lowering intraocular pressure in a subject in need of such treatment, which comprises administering a therapeutically effective amount of a composition comprising ester pro-drugs of (R) [3-(1-(1H-imidazol-4-yl)ethyl)-2-methylphenyl]methanol, or pharmaceutical compositions containing them. Upon hydrolytic and/or enzymatic cleavage of the ester functionality the parent compound (R) [3-(1-(1H-imidazol-4-yl)ethyl)-2-methylphenyl]methanol, is released to act as a selective modulator of the alpha 2 adrenergic receptors.

The ester pro-drugs of [3-(1-(1H-imidazol-4-yl)ethyl)-2-methylphenyl]methanol are useful for the treatment or prevention of mammals, including humans, in a range of conditions and diseases that are alleviated by alpha 2A, 2B, 2C activation, including but not limited to treating or preventing glaucoma, elevated intraocular pressure, ischemic neuropathies, optic neuropathy, pain, visceral pain, corneal pain, headache pain, migraine, cancer pain, back pain, irritable bowel syndrome pain, muscle pain and pain associated with diabetic neuropathy, the treatment of diabetic retinopathy, other retinal degenerative conditions, stroke, cognitive deficits, neuropsychiatric conditions, drug dependence and addiction, withdrawal of symptoms, obsessive-compulsive disorders, obesity, insulin resistance, stress-related conditions, diarrhea, diuresis, nasal congestion, spasticity, attention deficit disorder, psychoses, anxiety, depression, autoimmune disease, Crohn's disease, gastritis, Alzheimer's, and Parkinson's ALS other neurodegenerative diseases, dermatological conditions, skin erythema (redness) and inflammation, acne, age related macular degeneration, wet macular degeneration, dry macular degeneration, geographic atrophy, diabetic macular edema, tumors, wound healing, inflammation and retinal vein occlusion, enhancing vision in patients with vision loss from conditions including glaucoma, retinitis pigmentosa and neuritis secondary to multiple sclerosis, rosacea (dilation of the blood vessels just under the skin), sunburn, chronic sun damage, discreet erythemas, psoriasis, acne rosacea, menopause-associated hot flashes, hot flashes resulting from orchiectomyatopic dermatitis, photoaging, seborrheic dermatitis, allergic dermatitis, redness of the skin, telangiectasia (dilations of previously existing small blood vessels) of the face, rhinophymia (hypertrophy of the nose with follicular dilation), red bulbous nose, acne-like skin eruptions (may ooze or crust), burning or stinging sensation of the face, irritated and bloodshot and watery eyes, erythema of the skin, cutenous hyperactivity with dilation of blood vessels of the skin, Lyell's syndrome, Stevens-Johnson syndrome, erythema multiforme minor, erythema multiforme major and other inflammatory skin diseases.

BRIEF DESCRIPTION OF THE DRAWINGS

FIG. 1 shows compound Isobutyric acid 3-[(S)-1-(1-isobutyryl-1H-imidazol-4-yl)-ethyl]-2-methyl-benzyl ester (Compound 1) has equal or comparable efficacy to Alphagan P® and has longer intraocular pressure duration than Alphagan P®.

DETAILED DESCRIPTION OF THE INVENTION

The present invention relates to a method of lowering intraocular pressure in a subject in need of such treatment, which comprises, consists essentially of, or consists of administering a therapeutically effective amount of a composition comprising ester pro-drugs of [3-(1-(1H-imidazol-4-yl)ethyl)-2-methylphenyl]methanol, ester pro-drugs of (S) [3-(1-(1H-imidazol-4-yl)ethyl)-2-methylphenyl]methanol or ester pro-drugs of (R) [3-(1-(1H-imidazol-4-yl)ethyl)-2-methylphenyl]methanol as alpha-2 agonists with therapeutic utility.

In a preferred embodiment the present invention relates to a method of lowering intraocular pressure in a subject in need of such treatment, which comprises, consists essentially of, or consists of administering a therapeutically effective amount of a composition comprising esters pro-drugs of (S)-[3-(1-(1H-imidazol-4-yl)ethyl)-2-methylphenyl]methanol as alpha-2 agonists with therapeutic utility. Upon hydrolytic or enzymatic cleavage of the ester functionality the parent compound, active metabolite, (S)-[3-(1-(1H-imidazol-4-yl)ethyl)-2-methylphenyl]methanol, is released to act as a selective modulator of the alpha 2 adrenergic receptors.

In one aspect of the invention, there is provided a method of lowering intraocular pressure in a patient in need thereof which comprises, consists essentially of or consists of administering a therapeutically effective amount of a pharmaceutical composition comprising, consisting essentially of or consisting of a therapeutically effective amount of ester pro-drugs of [3-(1-(1H-imidazol-4-yl)ethyl)-2-methylphenyl]methanol, or the enantiomers thereof, or the tautomers thereof, or pharmaceutically acceptable salts thereof.

In another aspect of the invention, there is provided a method of lowering intraocular pressure in a patient in need thereof which comprises, consists essentially of or consists of administering a therapeutically effective amount of a pharmaceutical composition comprising, consisting essentially of or consisting of a therapeutically effective amount of ester pro-drugs of (S) [3-(1-(1H-imidazol-4-yl)ethyl)-2-methylphenyl]methanol, or the tautomers thereof, or pharmaceutically acceptable salts thereof.

In another aspect of the invention, there is provided a method of lowering intraocular pressure in a patient in need thereof which comprises, consists essentially of or consists of administering a therapeutically effective amount of a pharmaceutical composition comprising, consisting essentially of or consisting of a therapeutically effective amount of ester pro-drugs of (R) [3-(1-(1H-imidazol-4-yl)ethyl)-2-methylphenyl]methanol, or the tautomers thereof, or pharmaceutically acceptable salts thereof.

In another aspect of the invention, there is provided a method of lowering intraocular pressure of a patient in need thereof which comprises, consists essentially of or consists of administering a therapeutically effective amount of a pharmaceutical composition comprising, consisting essentially of or consisting of a therapeutically effective amount of ester pro-drugs of [3-(1-(1H-imidazol-4-yl)ethyl)-2-methylphenyl]methanol, or the enantiomers thereof, or the tautomers thereof, or pharmaceutically acceptable salts thereof, to the affected eye of said patient, as a single dose, wherein the affected eye maintains an intraocular pressure less than the baseline intraocular pressure for at least eight (8) hours and preferably at least ten (10) hours and more preferably at least twelve (12) hours, from the time of administration.

The term "baseline", as used herein, refers to the intraocular pressure measurement taken for the untreated eye.

The term "subject", as used herein, refers to a human patient.

In a still further aspect of the invention, there is provided a method of lowering intraocular pressure of a patient in need thereof which comprises administering a therapeutically effective amount of a composition comprising ester pro-drugs of [3-(1-(1H-imidazol-4-yl)ethyl)-2-methylphenyl]methanol, or the enantiomers thereof, or the tautomers thereof, or pharmaceutically acceptable salts thereof, to the affected eye of said patient, once or twice daily, preferably once daily, wherein the affected eye maintains an intraocular pressure less than the baseline intraocular pressure, throughout the day.

In another aspect of the invention, there is provided a method of lowering intraocular pressure of a patient in need thereof which comprises, consists essentially of or consists of administering a therapeutically effective amount of a pharmaceutical composition comprising, consisting essentially of or consisting of a therapeutically effective amount of ester pro-drugs of (S) [3-(1-(1H-imidazol-4-yl)ethyl)-2-methylphenyl]methanol, or the tautomers thereof, or pharmaceutically acceptable salts thereof, to the affected eye of said patient, as a single dose, wherein the affected eye maintains an intraocular pressure less than the baseline intraocular pressure for at least eight (8) hours and preferably at least ten (10) hours and more preferably at least twelve (12) hours, from the time of administration.

In a still further aspect of the invention, there is provided a method of lowering intraocular pressure of a patient in need thereof which comprises administering a therapeutically effective amount of a composition comprising ester pro-drugs of (S) [3-(1-(1H-imidazol-4-yl)ethyl)-2-methylphenyl]methanol, or the tautomers thereof, or pharmaceutically acceptable salts thereof, to the affected eye of said patient, once or twice daily, preferably once daily, wherein the affected eye maintains an intraocular pressure less than the baseline intraocular pressure, throughout the day.

In another aspect of the invention, there is provided a method of lowering intraocular pressure of a patient in need thereof which comprises, consists essentially of or consists of administering a therapeutically effective amount of a pharmaceutical composition comprising, consisting essentially of or consisting of a therapeutically effective amount of ester pro-drugs of (R) [3-(1-(1H-imidazol-4-yl)ethyl)-2-methylphenyl]methanol, or the tautomers thereof, or pharmaceutically acceptable salts thereof, to the affected eye of said patient, as a single dose, wherein the affected eye maintains an intraocular pressure less than the baseline intraocular pressure for at least eight (8) hours and preferably at least ten (10) hours and more preferably at least twelve (12) hours, from the time of administration.

In a still further aspect of the invention, there is provided a method of lowering intraocular pressure of a patient in need thereof which comprises administering a therapeutically effective amount of a composition comprising ester pro-drugs of (R) [3-(1-(1H-imidazol-4-yl)ethyl)-2-methylphenyl]methanol, or the tautomers thereof, or pharmaceutically acceptable salts thereof, to the affected eye of said patient, once or twice daily, preferably once daily, wherein the affected eye maintains an intraocular pressure less than the baseline intraocular pressure, throughout the day.

"Prodrugs" are frequently referred to by the term "metabolically cleavable derivatives" which refers to compound forms which are rapidly transformed in vivo to the parent compound according to the invention, for example, by hydrolysis in blood. Thus, prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Such metabolically cleavable groups form a class well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialklysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. (T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987).

In one aspect, the invention therefore relates to a method of lowering intraocular pressure in a subject in need of such treatment, which comprises administering a therapeutically effective amount of a composition comprising a compound having Formula I, its individual enantiomers, its individual diastereoisomers, its individual hydrates, its individual solvates, its individual crystal forms, its individual isomers, its individual tautomers or a pharmaceutically acceptable salt thereof,

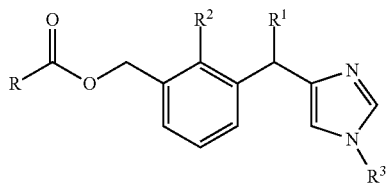

Formula I wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

In a preferred aspect, the invention therefore relates to a method of lowering intraocular pressure in a subject in need of such treatment, which comprises administering a therapeutically effective amount of a composition comprising a compound having Formula II, its individual diastereoisomers, its individual hydrates, its individual solvates, its individual crystal forms, its individual isomers, its individual tautomers or a pharmaceutically acceptable salt thereof,

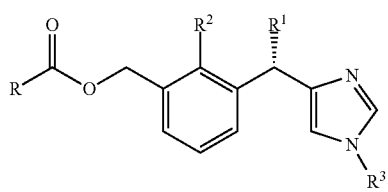

Formula II wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

In another aspect, the invention therefore relates to a method of lowering intraocular pressure in a subject in need of such treatment, which comprises administering a therapeutically effective amount of a composition comprising a compound having Formula III, its individual diastereoisomers, its individual hydrates, its individual solvates, its individual crystal forms, its individual isomers, its individual tautomers or a pharmaceutically acceptable salt thereof,

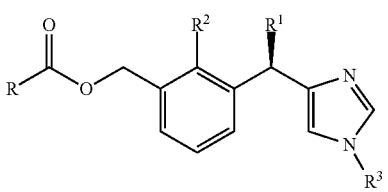

Formula III wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

The following paragraphs provide definitions of the various chemical moieties that make up the compounds of the invention and are intended to apply uniformly throughout the specification and claims unless expressly stated otherwise.

The term "alkyl" as used herein, is defined as including a saturated monovalent alkane moiety having straight or branched alkane moieties or combinations thereof and containing 1-10 carbon atoms, preferably 1-8 carbon atoms and more preferably 1-4 carbon atoms. Alkyl moieties can optionally be substituted by, but not limited to, amino groups, aryl groups, halogens. One methylene (—$CH_2$—) group can be replaced by carbonyl, —NH—, carboxyl, amide, sulfur or by oxygen. Examples include, but are not limited to, methyl, ethyl, propyl, butyl, sec-butyl, pentyl, iso-pentyl, neo-pentyl, hexyl, iso-hexyl, 3-methyl-butyl, 2-amino-N-isobutyl acetamide, iso-butyl, tert-butyl, iso-propyl, ethylphenyl, methylphenyl, 2-amino-3-methyl-butanamide-N-2-methyl-1-propyl, 1-amino-2-methyl-prop-1-yl.

The term "heterocycle" as used herein is defined as an aromatic or non aromatic 5 to 10 membered monocyclic or bicyclic ring containing at least one heteroatom selected from O or N or S or combinations thereof, interrupting the carbocyclic ring structure. Heterocycles can optionally be substituted by, but not limited to, $C_{1-6}$ alkyl, amino, halogen, —O($C_{1-6}$ alkyl), —OC(O)($C_{1-6}$ alkyl), —O(O)O($C_{1-6}$ alkyl), —NHC(O)($C_{1-6}$ alkyl), —C(O)NH($C_{1-6}$alkyl), —S($C_{1-6}$ alkyl) groups. Examples include, but are not limited to, furyl, pyrryl, pyridyl, pyrimidyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, 1,2,4-thiadiazolyl, isooxazolyl, quinazolinyl, pyridazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, pyrrolidinyl, piperidinyl and piperazinyl.

The term "aryl" as used herein, is defined as including an organic moiety derived from an aromatic hydrocarbon consisting of a monocyclic or bicyclic ring containing 6-10 carbon atoms by removal of one hydrogen atom, such as phenyl or naphtyl. Aryl groups can optionally be substituted by, but not limited to, $C_{1-6}$ alkyl, amino, halogen, —O($C_{1-6}$ alkyl), —OC(O)($C_{1-6}$ alkyl), —O(O)O($C_{1-6}$ alkyl), —NHC(O)($C_{1-6}$ alkyl), —C(O)NH($C_{1-6}$ alkyl), —S($C_{1-6}$ alkyl) groups. Examples include, but are not limited to, phenyl, naphtyl.

The term "H" as used herein refers to a hydrogen atom.
The term "O" as used herein refers to an oxygen atom.
The term "S" as used herein refers to a sulfur atom.
The term "N" as used herein refers to a nitrogen atom.
The term "amino" as used herein refers to a group of formula —$NH_2$.
The term "amide" as used herein refers to a group of formula —O(O)NH— or —NHC(O)—.
The term "halogen", as used herein refers to an atom of chlorine, bromine, iodine or fluorine.
The term "carbonyl" as used herein refers to a group of formula —C═O.
The term "carboxyl", as used herein refers to a group of formula —C(O)O— or —OC(O)—.

Generally $R^1$ is H or $C_{1-3}$ alkyl. Preferred $R^1$ is $C_{1-3}$ alkyl. Most preferred $R^1$ is methyl.

Generally $R^2$ is H or $C_{1-3}$ alkyl. Preferred $R^2$ is $C_{1-3}$ alkyl. Most preferred $R^2$ is methyl.

Generally $R^3$ is H, $C_{1-10}$ alkyl, heterocycle or aryl. Preferred $R^3$ is H, phenyl or $C_{1-10}$ alkyl. Most preferred $R^3$ is H.

Generally R is $C_{1-10}$ alkyl, heterocycle or aryl. Preferred R is methyl, iso-butyl, tert-butyl, iso-propyl, ethylphenyl, phenyl, 2-amino-1-phenylethyl, 2-(2-amino-3-methyl-butyrylamino)-2-methyl-prop-1-yl, 1-amino-2-methyl-prop-1-yl, 2-(2-amino-acetylamino)-2-methyl-prop-1-yl. Most preferred R groups are tert-butyl, iso-propyl.

As used herein, "tautomer" refers to the migration of protons between adjacent single and double bonds. The tautomerization process is reversible. Compounds described herein can undergo any possible tautomerization that is within the physical characteristics of the compound. The following is a tautomerization example that can occur in compounds described herein:

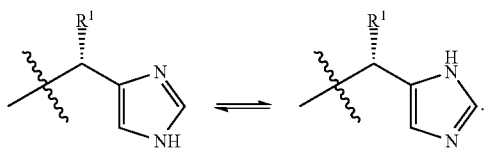

Compounds of the invention are:
iso-Butyric acid 3-[(S)-1-(1H-imidazol-4-yl)ethyl]-2-methyl-benzyl ester;
2,2-Dimethyl-propionic acid 3-[(S)-1-(1H-imidazol-4-yl)ethyl]-2-methyl-benzyl ester;
Acetic acid 3-[(S)-1-(1H-imidazol-4-yl)ethyl]-2-methyl-benzyl ester;
Benzoic acid 3-[(S)-1-(1H-imidazol-4-yl)-ethyl]-2-methyl-benzyl ester;
3-Methyl-butyric acid 3-[(S)-1-(1H-imidazol-4-yl)-ethyl]-2-methyl-benzyl ester;
3-Phenyl-propionic acid 3-[(S)-1-(1H-imidazol-4-yl)-ethyl]-2-methyl-benzyl ester;
2-Amino-3-methyl-butyric acid 3-[(S)-1-(1H-imidazol-4-yl)-ethyl]-2-methyl-benzyl ester;
2-(2-Amino-3-methyl-butyrylamino)-3-methyl-butyric acid 3-[(S)-1-(1H-imidazol-4-yl)-ethyl]-2-methyl-benzyl ester;
2-(2-Amino-acetylamino)-3-methyl-butyric acid 3-[(S)-1-(1H-imidazol-4-yl)-ethyl]-2-methyl-benzyl ester;
2-Amino-3-phenyl-propionic acid 3-[(S)-1-(1H-imidazol-4-yl)-ethyl]-2-methyl-benzyl ester.

Intermediates of the invention are:
iso-Butyric acid 3-[(S)-1-(1-iso-butyryl-1H-imidazol-4-yl)-ethyl]-2-methyl-benzyl ester;
2,2-Dimethyl-propionic acid 3-{(S)-1-[1-(2,2-dimethyl-propionyl)-1H-imidazol-4-yl]-ethyl}-2-methyl-benzyl ester;
Acetic acid 3-[(S)-1-(1-acetyl-1H-imidazol-4-yl)-ethyl]-2-methyl-benzyl ester;
Benzoic acid 3-[(S)-1-(1-benzoyl-1H-imidazol-4-yl)-ethyl]-2-methyl-benzyl ester;
3-Methyl-butyric acid 2-methyl-3-{(S)-1-[1-(3-methyl-butyryl)-1H-imidazol-4-yl]-ethyl}-benzyl ester;
Phenyl-propionic acid 2-methyl-3-{(S)-1-[1-(3-phenyl-propionyl)-1H-imidazol-4-yl]-ethyl}-benzyl ester;
2-tert-Butoxycarbonylamino-3-methyl-butyric acid 3-{(S)-1-[1-(2-tert-butoxy carbonylamino-3-methyl-butyryl)-1H-imidazol-4-yl]-ethyl}-2-methyl-benzyl ester;
2-tert-Butoxycarbonylamino-3-methyl-butyric acid 3-[(S)-1-(1H-imidazol-4-yl)-ethyl]-2-methyl-benzyl ester;
2-(2-tert-Butoxycarbonylamino-3-methyl-butyrylamino)-3-methyl-butyric acid 3-{(S)-1-[1-(2-tert-butoxycarbonylamino-3-methyl-butyryl)-1H-imidazol-4-yl]-ethyl}-2-methyl-benzyl ester;
2-(2-tert-Butoxycarbonylamino-3-methyl-butyrylamino)-3-methyl-butyric acid 3-[(S)-1-(1H-imidazol-4-yl)-ethyl]-2-methyl-benzyl ester;
2-(2-tert-Butoxycarbonylamino-acetylamino)-3-methyl-butyric acid 3-[(S)-1-(1H-imidazol-4-yl)-ethyl]-2-methyl-benzyl ester;
2-tert-Butoxycarbonylamino-3-phenyl-propionic acid 3-[(S)-1-(1H-imidazol-4-yl)-ethyl]-2-methyl-benzyl ester.

Some compounds of Formula I, Formula II and Formula III and some of their intermediates have at least one stereogenic center in their structure. This stereogenic center may be present in an (R) or (S) configuration, said (R) and (S) notation is used in correspondence with the rules described in Pure Appli. Chem. (1976), 45, 11-13.

Compounds according to the present invention may exist in different polymorphic forms. Although not explicitly indicated in the above formula, such forms are intended to be included within the scope of the present invention.

Compounds of Formula I, Formula II or Formula III and their salts can be in the form of a solvate, which is included within the scope of the present invention. Such solvates include for example hydrates, alcoholates and the like.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I, Formula II or Formula III are able to form. The acid addition salt form of a compound of Formula I, Formula II or Formula III that occurs in its free form as a base can be obtained by treating the free base with an appropriate acid such as an inorganic acid, for example but not limited to, hydrochloric acid, hydrobromic acid, sulfuric acid, phosphoric acid, nitric acid and the like; or an organic acid such as for example but not limited to, as citric acid, acetic acid, oxalic acid, tartaric acid, succinic acid, malic acid, fumaric acid, ascorbic acid, benzoic acid, tannic acid, palmoic acid, alginic acid, polyglutamic acid, naphthalenesulfonic acid, napthalenedisulfonic, and polygalacturonic acid as well as base addition salts such as those formed with alkali- and alkaline earth metals such as sodium, potassium and calcium and the like (Handbook of Pharmaceutical Salts, P. Heinrich Stahal & Camille G. Wermuth (Eds), Verlag Helvetica Chemica Acta-Zürich, 2002, 329-345).

The compounds can also be administered as pharmaceutically acceptable quaternary salts known by those skilled in the art, which specifically include, but not limiting to the quaternary ammonium salt of the formula —NY$^+$Z$^-$, wherein Y is hydrogen, alkyl, or benzyl, and Z is a counterion, including but not limited to, chloride, bromide, iodide, —O-alkyl, toluenesulfonate, methylsulfonate, sulfonate, phosphate, or carboxylate (such as fumarate, benzoate, succinate, acetate, glycolate, maleate, malate, fumarate, citrate, tartrate, ascorbate, benzoate, cinnamoate, mandeloate, benzyloate, and diphenylacetate).

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual nontoxic, pharmaceutically acceptable carriers for tablets, pellets, capsules, suppositories, solutions, emulsions, suspensions, and any other form suitable for use. The carriers which can be used include but are not limited to, glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The present invention concerns also the use of a compound of Formula I, Formula II or Formula III, or a pharmaceutically acceptable salt thereof, for the manufacture of a medicament for the therapeutic application. The present invention concerns also the a method for manufacturing a medicament intended for therapeutic application wherein a compound having general Formula I, Formula II or Formula III, or a pharmaceutically active derivative or salt thereof is used.

Since individual subjects may present a wide variation in severity of symptoms and each drug has its unique therapeutic characteristics, the precise mode of administration and dosage employed for each subject is left to the discretion of the practitioner. The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. The actual amount of the compound to be administered in any given case will be determined by a physician taking into account the relevant circumstances, such as the severity of the condition, the age and weight of the patient, the patient's general physical condition, the cause of the condition, and the route of administration. Additionally, the formulations may be designed to delay release of the active compound over a given period of time, or to carefully control the amount of drug released at a given time during the course of therapy.

Ester pro-drugs of [3-(1-(1H-imidazol-4-yl)ethyl)-2-methylphenyl]methanol, of (S) [3-(1-(1H-imidazol-4-yl)ethyl)-2-methylphenyl]methanol or of (R) [3-(1-(1H-imidazol-4-yl)ethyl)-2-methylphenyl]methanol and their pharmaceutically-acceptable salts may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. Pat. No. 7,931,909 which is hereby incorporated by reference. Such biocompatible intraocular implants include ester pro-drugs of [3-(1-(1H-imidazol-4-yl)ethyl)-2-methylphenyl]methanol, of (S) [3-(1-(1H-imidazol-4-yl)ethyl)-2-methylphenyl]methanol or of (R) [3-(1-(1H-imidazol-4-yl)ethyl)-2-methylphenyl]methanol and a polymer associated with ester pro-drugs of [3-(1-(1H-imidazol-4-yl)ethyl)-2-methylphenyl]methanol, of (S) [3-(1-(1H-imidazol-4-yl)ethyl)-2-methylphenyl]methanol or of (R) [3-(1-(1H-imidazol-4-yl)ethyl)-2-methylphenyl]methanol to facilitate release thereof into an eye for an extended period of time. Ophthalmic formulations of drug products are well known in the art and described in, for example, U.S. Patent Application Publication No. 20050059583; No. 20050277584; U.S. Pat. No. 7,297,679; and No. 20070015691; and U.S. Pat. Nos. 5,474,979 and 6,582,718, the disclosures of all which are incorporated herein by reference. The ester pro-drugs of [3-(1-(1H-imidazol-4-yl)ethyl)-2-methylphenyl]methanol, of (S) [3-(1-(1H-imidazol-4-yl)ethyl)-2-methylphenyl]methanol or of (R) [3-(1-(1H-imidazol-4-yl)ethyl)-2-methylphenyl]methanol may be formulated with efficacy enhancing components as disclosed in U.S. Pat. No. 7,491,383 B2, which is hereby incorporated by reference in its entirety.

In one method of the invention, said intraocular pressure is lowered for at least eight (8) hours subsequent to administration.

In a preferred method of the invention, said intraocular pressure is lowered for at least ten (10) hours subsequent to administration.

In a more preferred method of the invention, said intraocular pressure is lowered for at least twelve (12) hours subsequent to administration.

In the method according to the present invention, the composition that is used, as a single dose, to lower intraocular pressure for at least eight (8) hours and preferably at least ten (10) hours and more preferably for at least twelve (12) hours, may comprise from 0.0005 to 5 percent, preferably from 0.005 to 2 percent, more preferably from 0.05 to 2 percent by weight of ester pro-drugs of [3-(1-(1H-imidazol-4-yl)ethyl)-2-methylphenyl]methanol, in a pharmaceutically-acceptable vehicle.

In another aspect of the invention, the method according to the present invention, the composition that is used, as a single dose, to lower intraocular pressure for at least eight (8) hours and preferably at least ten (10) hours and more preferably for at least twelve (12) hours, may comprise from 0.01 to 5 percent, preferably from 0.01 to 2 percent, more preferably from 0.05 to 2 percent by weight of ester pro-drugs of (S) [3-(1-(1H-imidazol-4-yl)ethyl)-2-methylphenyl]methanol in a pharmaceutically-acceptable vehicle.

In another aspect of the invention, the method according to the present invention, the composition that is used, as a single dose, to lower intraocular pressure for at least eight (8) hours and preferably at least ten (10) hours and more preferably for at least twelve (12) hours, may comprise from 0.01 to 5 percent, preferably from 0.01 to 2 percent, more preferably from 0.05 to 2 percent by weight of ester pro-drugs of (R) [3-(1-(1H-imidazol-4-yl)ethyl)-2-methylphenyl]methanol in a pharmaceutically-acceptable vehicle.

In forming compositions for topical administration, the pharmaceutical compositions are preferably formulated as a solution in water at a pH of 5.5 to 8.0, e.g. about 6.9. Said composition is preferably formulated as an eye drop suitable for topical administration. While the precise regime is left to the discretion of the clinician, it is recommended that the solution be topically applied by placing one drop in each eye one or two times, preferably once a day. Other ingredients which may be desirable to use in the ophthalmic preparations used in the method of the present invention include preservatives, co-solvents and viscosity building agents; bodium chloride, potassium chloride, calcium chloride dihydrate, magnesium chloride hexahydrate, boric acid and sodium borate decahydrate (as buffering agents) and purified water (*Clinical Ocular Pharmacology* By Jimmy D. Bartlett, Siret D. Jaanus, 2008, p 266). Preservatives are thus required to prevent microbial contamination during use. Suitable preservatives include: stabilized oxychloro complex (sold under the trademark Purite™), stabilized chlorine dioxide, benzalkonium chloride, thimerosal, chlorobutanol, methyl paraben, propyl paraben, phenylethyl alcohol, edetate disodium, sorbic acid, Onamer M, or other agents known to those skilled in the art (*Review of Ophthalmology*, June 2001, Robert Noecker, Md.). A common side-effect of these preservatives is burning.

Typically, for the compositions utilized in the method of the present invention, the effective concentration of the preservative will range from 0.001% to 1%, preferably from 0.01% to 0.5%, by weight. In particular stabilized oxychloro complex (Purite®) will range from 0.001 to 0.01%, by weight.

The solubility of the components of the present compositions may be enhanced by a surfactant or other appropriate co-solvent in the composition. Such cosolvents include polysorbate 20, 60, and 80, Pluronic® F-68, F-84 and P-103, cyclodextrin, Solutol, or other agents known to those skilled in the art. Typically such co-solvents are employed at a level of from 0.01% to 2% by weight.

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity building agents include as examples polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01% to 2% by weight.

The following formulations are representative ophthalmic compositions of the invention for topical use when indicated for treating elevated intraocular pressure associated with glaucoma. In one example, the free base of ester pro-drugs of [3-(1-(1H-imidazol-4-yl)ethyl)-2-methylphenyl]methanol, or the free base of ester pro-drugs of (S) [3-(1-(1H-imidazol-4-yl)ethyl)-2-methylphenyl]methanol or the free base of ester pro-drugs of (R) [3-(1-(1H-imidazol-4-yl)ethyl)-2-methylphenyl]methanol was dissolved in sterile distilled water, hydrochloric acid was added and the hydrochloric salt of the compound was formed in situ. The solution was titrated with sodium hydroxide until the pH of the solution reached 8.0. The final concentration of ester pro-drugs of [3-(1-(1H-imidazol-4-yl)ethyl)-2-methylphenyl]methanol, or of ester pro-drugs of (S) [3-(1-(1H-imidazol-4-yl)ethyl)-2-methylphenyl]methanol or of ester pro-drugs of (R) [3-(1-(1H-imidazol-4-yl)ethyl)-2-methylphenyl]methanol is 1% by weight. In another example, the free base of ester pro-drugs of [3-(1-(1H-imidazol-4-yl)ethyl)-2-methylphenyl]methanol, or the free base of ester pro-drugs of (S) [3-(1-(1H-imidazol-4-yl)ethyl)-2-methylphenyl]methanol or the free base of ester pro-drugs of (R) [3-(1-(1H-imidazol-4-yl)ethyl)-2-methylphenyl]methanol was dissolved in sterile distilled water with boric acid, benzalkonium chloride and glycerin.

With respect to the present invention reference to a compound or compounds, is intended to encompass that compound in each of its possible isomeric forms and mixtures thereof unless the particular isomeric form is referred to specifically.

The present invention also concerns a process for preparing the compounds having general Formula I, Formula II or Formula III.

The synthetic scheme set forth below, illustrates how compounds according to the invention can be made. Those skilled in the art will be able to routinely modify and/or adapt the following scheme to synthesize any compounds of the invention covered by Formula I, Formula II or Formula III.

General scheme for synthesizing ester prodrugs of (S)-[3-(1-(1H-imidazol-4-yl)ethyl)-2-methylphenyl]methanol

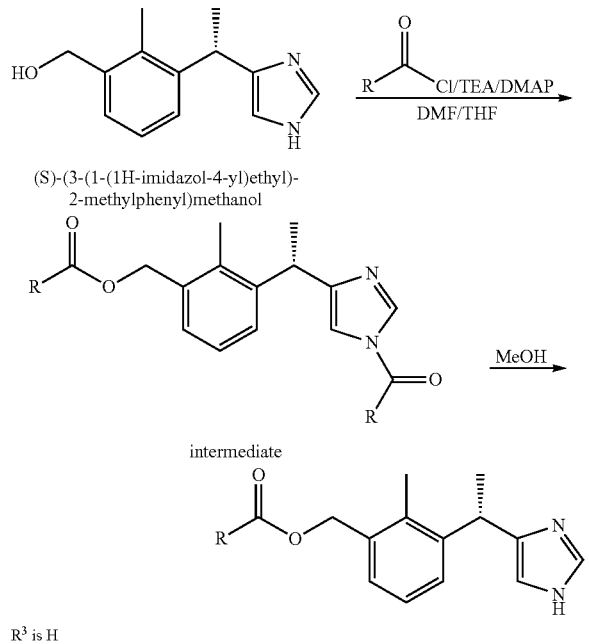

$R^3$ is H

In a first step (S)-[3-(1-(1H-imidazol-4-yl)ethyl)-2-methylphenyl]methanol (CAS 189255-79-6) can react with the desired acyl chloride, in the presence of N,N-dimethyl formamide (DMF), tertahydrofuran (THF), triethylamine (TEA) and 4-dimethyl aminopyridine (DMAP). After a typical work-up by extraction, the residue can be purified by medium pressure liquid chromatography (MPLC) (0% to 40% ethyl acetate in hexanes) to yield the intermediate compound as solid.

In a second step, the intermediate obtained in the first reaction, can react with methanol (MeOH). The residue can be purified by MPLC (50% ethyl acetate in hexanes then 5% 7N ammonia/methanol/dichloromethane) to yield the desired compound as a solid.

It is to be understood that both the foregoing general description and the following detailed description are exemplary and explanatory only and are not restrictive of the invention claimed. As used herein, the use of the singular includes the plural unless specifically stated otherwise.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

The IUPAC names of the compounds mentioned in the examples were generated with ACD version 8.

Unless specified otherwise in the examples, characterization of the compounds is performed according to the following methods:

NMR spectra are recorded on 300 MHz Varian and acquired at room temperature. Chemical shifts are given in ppm referenced either to internal TMS or to the residual solvent signal.

All the reagents, solvents, catalysts for which the synthesis is not described are purchased from chemical vendors such as Sigma Aldrich, Fluka, Lancaster, however some known reaction intermediates, for which the CAS registry number is mentioned, were prepared in-house following known procedures. Usually the compounds of the invention were purified by flash column chromatography.

The following abbreviations are used in the examples:

| | |
|---|---|
| DCM | dichloromethane |
| MeOH | methanol |
| CD$_3$OD | deuterated methanol |
| NH$_3$ | ammonia |
| Na$_2$SO$_4$ | sodium sulfate |
| DMF | N,N-dimethylformamide |
| MgSO$_4$ | magnesium sulfate |
| EtOAc | ethylacetate |
| i-PrOH | iso-propanol |
| CDCl$_3$ | deuterated chloroform |
| MPLC | medium pressure liquid chromatography |
| DMF | dimethylformamide |
| TEA | triethylamine |
| THF | tertahydrofuran |
| DMAP | 4-dimethylaminopyridine |
| RT | room temperature |
| Boc-L-Valine | N-(tert-Butoxycarbonyl)-L-valine |
| Boc-Glycine | N-(tert-Butoxycarbonyl) glycine |
| Boc-L-Phenylalanine | N-(tert-Butoxycarbonyl)-L-phenylalanine |
| HCl | hydrochloric acid |
| H$_2$O | water |
| EDCl | 1-ethyl-3-(3-dimethylaminopropyl) carbodiimide |
| NaHCO$_3$ | sodium bicarbonate |

Example 1

Intermediate 1 iso-Butyric acid 3-[(S)-1-(1-isobutyryl-1H-imidazol-4-yl)-ethyl]-2-methyl-benzyl ester To a solution of (S)-[3-(1-(1H-imidazol-4-yl)ethyl)-2-methylphenyl]methanol (1.34 g, 6.2 mmol) in DMF (8 ml) and THF (50 ml), were added TEA (3.5 ml, 24.8 mmol), DMAP (780 mg, 6.2 mmol) and iso-butyryl chloride (2.18 g, 20.5 mmol). The resulting mixture was stirred at RT for 16 h, quenched with H$_2$O and extracted with ethyl acetate. The combined organic layers were washed with brine, and dried over Na$_2$SO$_4$, and concentrated under reduced pressure. The residue was purified by MPLC (0% to 40% ethyl acetate in hexanes) to yield Intermediate 1 as a solid.

$^1$H-NMR (CD$_3$OD, δ ppm): 1.15 (d, J=7.03 Hz, 6H), 1.26 (d, 6H, J=6.74 Hz), 1.56 (d, J=7.03 Hz, 3H), 2.34 (s, 3H), 2.58 (hept, J=7.03 Hz, 1H), 3.34 (hept, J=7.74 Hz, 1H), 4.42 (q, J=7.03 Hz, 1H), 5.15 (s, 2H), 7.07-7.10 (m, 2H), 7.12-7.15 (m, 1H), 7.31 (s, 1H), 8.35 (s, 1H).

Intermediates 2-6 were prepared in a similar manner to the method described in Example 1 starting with (S)-[3-(1-(1H-imidazol-4-yl)ethyl)-2-methylphenyl]methanol. The acyl chloride used in each case and the results are tabulated below in Table 1.

TABLE 1

| Intermediate number | IUPAC name | Acyl chloride | $^1$NMR (Solvent; δ ppm) |
|---|---|---|---|
| 2 | 2,2-Dimethyl-propionic acid 3-{(S)-1-[1-(2,2-dimethyl-propionyl)-1H-imidazol-4-yl]-ethyl}-2-methyl-benzyl ester | Pivaloyl chloride | (CD$_3$OD): 1.19 (s, 9H), 1.42 (s, 9H), 1.56 (d, J = 7.03 Hz, 3H), 2.34 (s, 3H), 4.42(q, J = 7.03 Hz, 1H), 5.15(s, 2H), 7.07-7.10 (m, 2H), 7.12-7.15 (m, 1H), 7.33 (s, 1H), 8.40 (s, 1H). |
| 3 | Acetic acid 3-[(S)-1-(1-acetyl-1H-imidazol-4-yl)-ethyl]-2-methyl-benzyl ester | Acetyl chloride | (CD$_3$OD): 1.55 (d, J = 7.03 Hz, 3H), 2.05 (s, 3H), 2.33 (s, 3H), 2.58 (s, 3H), 4.39(q, J = 7.03 Hz, 1H), 5.15(s, 2H), 7.07-7.10 (m, 2H), 7.12-7.15 (m, 1H), 7.30 (s, 1H), 8.29 (s, 1H). |
| 4 | Benzoic acid 3-[(S)-1-(1-benzoyl-1H-imidazol-4-yl)-ethyl]-2-methyl-benzyl ester: | Benzoyl chloride | (CD$_3$OD): 1.58 (d, J = 7.03 Hz, 3H), 2.43 (s, 3H), 4.46(q, J = 7.03 Hz, 1H), 5.41 (s, 2H), 7.11-7.18 (m, 2H), 7.27-7.35 (m, 2H), 7.42-7.50 (m, 2H), 7.50-7.63 (m, 3H), 7.65-7.71 (m, 1H), 7.79 (d, J = 7.33 Hz, 2H), 8.00 (d, J = 7.33 Hz, 2H), 8/09 (s, 1H). |
| 5 | 3-Methyl-butyric acid 2-methyl-3-{(S)-1-[1-(3-methyl-butyryl)-1H-imidazol-4-yl]ethyl}-benzyl ester | Methyl-butanoyl chloride | (CD$_3$OD): 0.91 (d, J = 6.44 Hz, 6H), 1.01 (d, J = 6.44 Hz, 6H), 1.54 (d, J = 7.03 Hz, 3H), 2.05 (hept, J = 6.44 Hz, 1H), 2.15-2.25 (m, 3H), 2.33 (s, 3H), 2.81 (d, J = 7.03 Hz, 3H), 4.42(q, J = 7.03 Hz, 1H), 5.14(s, 2H), 7.07-7.19 (m, 3H), 7.28 (s, 1H), 8.32 (s, 1H). |
| 6 | 3-Phenyl-propionic acid 2-methyl-3-{(S)-1-[1-(3-phenyl-propionyl)-1H-imidazol-4-yl]ethyl}-benzyl ester | Phenyl-propanoyl chloride | (CD$_3$OD): 1.52 (d, J = 7.03 Hz, 3H), 2.24 (s, 3H), 2.64 (t, J = 7.61 Hz, 2H), 2.90 (t, J = 7.61 Hz, 2H), 3.04 (t, J = 7.61 Hz, 2H), 3.24 (t, J = 7.61 Hz, 2H), 4.34 (q, J = 7.03 Hz, 1H), 5.13 (s, 2H), 7.08-7.248 (m, 14H), 8.25 (s, 1H). |

Example 2

Compound 1 iso-Butyric acid 3-[(S)-1-(1H-imidazol-4-yl)-ethyl]-2-methyl-benzyl ester

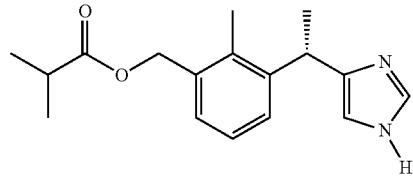 [SMILES: Cc1c(COC(=O)C(C)C)cccc1[C@H](C)c1c[nH]cn1]

Intermediate 1 was dissolved in MeOH (50 ml) and the mixture was stirred at RT for 24 h and then concentrated under reduced pressure. The residue was purified by MPLC (50% ethyl acetate in hexanes then 5% 7N NH$_3$/MeOH/DCM) to yield Compound 1 as a solid.

$^1$H-NMR (CD$_3$OD; δ ppm): 1.15 (d, J=7.03 Hz, 6H), 1.54 (d, J=7.03 Hz, 3H), 2.33 (s, 3H), 2.56 (hept, J=7.03 Hz, 1H), 4.42 (q, J=7.03 Hz, 1H), 5.15 (s, 2H), 6.70 (s, 1H), 7.07-7.10 (m, 2H), 7.12-7.15 (m, 1H), 7.55 (s, 1H).

Compounds 2-6 and of the invention were prepared according to the procedure described in Example 2, by reacting the corresponding intermediate with methanol. The results are tabulated below in Table 2.

TABLE 2

| Comp. No. | IUPAC name Structure | Inter. No. | $^1$NMR (Solvent, δ ppm) |
|---|---|---|---|
| 2 | 2,2-Dimethyl-propionic acid 3-[(S)-1-(1H-imidazol-4-yl)-ethyl]-2-methyl-benzyl ester | 2 | (CD$_3$OD): 1.19 (s, 9H), 1.54 (d, J = 7.03 Hz, 3H), 2.33 (s, 3H), 4.42 (q, J = 7.03 Hz, 1H), 5.13 (s, 2H), 6.70 (s, 1H), 7.07-7.10 (m, 2H), 7.12-7.15 (m, 1H), 7.55 (s, 1H). |
| 3 | Acetic acid 3-[(S)-1-(1H-imidazol-4-yl)-ethyl]-2-methyl-benzyl ester | 3 | (CD$_3$OD): 1.54 (d, J = 7.03 Hz, 3H), 2.04 (s, 3H), 2.33 (s, 3H), 4.42 (q, J = 7.03 Hz, 1H), 5.13 (s, |

| Comp. No. | IUPAC name Structure | Inter. No. | ¹NMR (Solvent, δ ppm) |
|---|---|---|---|
|  | 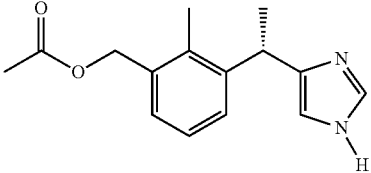 [SMILES: CC(=O)OCc1cccc([C@H](C)c2c[nH]cn2)c1C] |  | 2H), 6.70 (s, 1H), 7.07-7.10 (m, 2H), 7.12-7.15 (m, 1H), 7.55 (s, 1H). |
| 4 | Benzoic acid 3-[(S)-1-(1H-imidazol-4-yl)-ethyl]-2-methyl-benzyl Ester 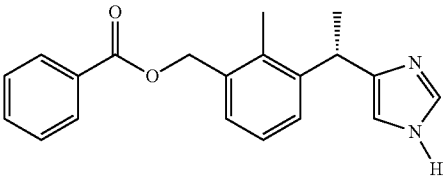 [SMILES: Cc1c(COC(=O)c2ccccc2)cccc1[C@H](C)c1c[nH]cn1] | 4 | (CD₃OD): 1.54 (d, J = 7.03 Hz, 3H), 2.31 (s, 3H), 4.42(q, J = 7.03 Hz, 1H), 5.13 (s, 2H), 6.70 (s, 1H), 7.07-7.15 (m, 2H), 7.25-7.28 (m, 1H), 7.54-7.47 (m, 2H), 7.55-7.60 (m, 2H), 8.0 (d, J = 7.33 Hz, 2H). |
| 5 | 3-Methyl-butyric acid 3-[(S)-1-(1H-imidazol-4-yl)-ethyl]-2-methyl-benzyl Ester 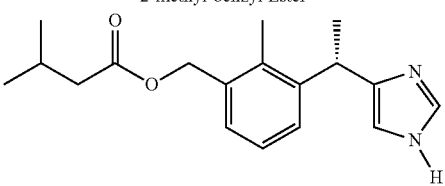 | 5 | (CD₃OD): 0.93 (d, J = 7.03 Hz, 6H), 1.54 (d, J = 7.03 Hz, 3H), 2.07 (hept, J = 7.03 Hz, 1H), 2.21 (d, J = 7.03 Hz, 2H), 2.33 (s, 3H), 4.42(q, J = 7.03 Hz, 1H), 5.15(s, 2H), 6.70 (s, 1H), 7.07-7.10 (m, 2H), 7.12-7.15 (m, 1H), 7.55 (s, 1H). |
| 6 | 3-Phenyl-propionic acid 3-[(S)-1-(1H-imidazol-4-yl)-ethyl]-2-methyl-benzyl Ester 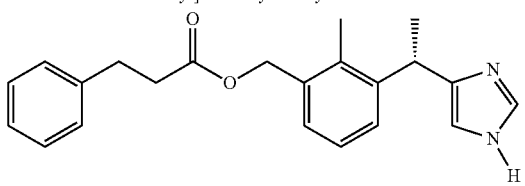 | 6 | (CD₃OD): 1.54 (d, J = 7.03 Hz, 3H), 2.23 (s, 3H), 2.65 (t, J = 7.61 Hz, 2H), 2.91 (t, J = 7.61 Hz, 2H), 4.40 (q, J = 7.03 Hz, 1H), 5.13 (s, 2H), 6.70 (s, 1H), 7.08-7.24 (m, 8H), 7.55 (s, 1H). |

Example 3

Intermediate 7

2-tert-Butoxycarbonylamino-3-methyl-butyric acid 3-{(S)-1-[1-(2-tert-butoxy carbonylamino-3-methyl-butyryl)-1H-imidazol-4-yl]-ethyl}-2-methyl-benzyl ester To a solution of (S)-[3-(1-(1H-imidazol-4-yl)ethyl)-2-methylphenyl]methanol (216 mg, 1.0 mmol) in DMF (2 ml) and THF (12 ml) were added EDCI (671 mg, 3.5 mmol), DMAP (427 mg, 3.5 mmol) and Boc-L-Valine (651 mg, 3.0 mmol). The mixture was stirred at RT for 16 h, quenched with H₂O and extracted with ethyl acetate. The combined organic layers were washed with H₂O, brine, and dried over Na₂SO₄, and concentrated under reduced pressure. The residue was purified by a column chromatography (30% ethyl acetate in hexanes) to yield Intermediate 7 as white solid.

¹H-NMR (CD₃OD; δ ppm): 0.85-1.01 (m, 12H), 1.20-1.48 (m, 18H), 1.56 (d, J=7.03 Hz, 3H), 2.01-2.20 (m, 2H), 2.35 (s, 3H), 4.03 (m, 1H), 4.42 (q, J=7.03 Hz, 1H), 4.60-4.65 (m, 1H), 5.15-5.29 (m, 2H), 7.10-7.20 (m, 2H), 7.20-7.25 (m, 1H), 7.33 (s, 1H), 8.44 (s, 1H).

Example 4

Intermediate 8

2-tert-Butoxycarbonylamino-3-methyl-butyric acid 3-[(S)-1-(1H-imidazol-4-yl)-ethyl]-2-methyl-benzyl ester The title compound was prepared from Intermediate 7 (600 mg, 0.98 mmol) in 30 ml of MeOH according to the procedure described in Example 2.

¹H-NMR (CD₃OD; δ ppm): 0.85-0.95 (m, 6H), 1.42 (m, 9H), 1.54 (d, J=7.03 Hz, 3H), 2.05 (m, 1H), 2.33 (s, 3H), 4.00 (d, J=6.15 Hz, 1H), 4.40 (q, J=7.03 Hz, 1H), 5.15-5.28 (m, 2H), 6.67 (s, 1H), 7.10-7.20 (m, 2H), 7.20-7.25 (m, 1H), 7.55 (s, 1H).

Example 5

Compound 7

2-Amino-3-methyl-butyric acid 3-[(S)-1-(1H-imidazol-4-yl)-ethyl]-2-methyl-benzyl ester

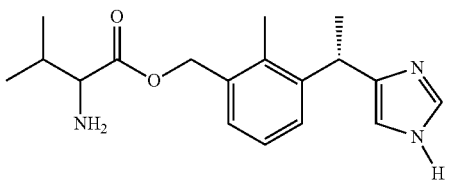 [SMILES: Cc1c(COC(=O)C(N)C(C)C)cccc1[C@H](C)c1c[nH]cn1]

To Intermediate 8 (390 mg, 0.94 mmol) was added 4N HCl in dioxane (8 ml). The resulting solution was stirred at RT for 4 hrs, then quenched with $H_2O$, neutralized with aqueous saturated $NaHCO_3$ and extracted with 25% isopropyl alcohol in chloroform. The combined organic layers were dried over $Na_2SO_4$, and concentrated under reduced pressure. The residue was purified by a column chromatography (5% 7N $NH_3$/MeOH in DCM) to yield Compound 7 as white solid.

$^1$H-NMR ($CD_3OD$; δ ppm): 0.85 (d, J=6.74 Hz, 3H), 0.91 (d, J=6.74 Hz, 3H), 1.54 (d, J=7.03 Hz, 3H), 1.96 (hept, J=6.74 Hz, 1H), 2.33 (s, 3H), 3.28 (d, J=6.74 Hz, 2H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

Example 6

Intermediate 9

2-(2-tert-Butoxycarbonylamino-3-methyl-butyrylamino)-3-methyl-butyric acid 3-{(S)-1-[1-(2-tert-butoxycarbonylamino-3-methyl-butyryl)-1H-imidazol-4-yl]-ethyl}-2-methyl-benzyl ester The title compound was prepared from Compound 7 (490 mg, 1.55 mmol), Boc-L-Valine (1.01 g, 4.67 mmol), EDCl (1.04 g, 5.42 mmol) and DMAP (671 mg, 5.5 mmol) according to the procedure described in Example 3.

$^1$H-NMR ($CD_3OD$; δ ppm): 0.85-0.92 (m, 12H), 1.43 (s, 9H), 1.55 (d, J=7.03 Hz, 1.97 (m, 1H), 2.14 (hept, J=6.60 Hz, 1H), 2.35 (s, 3H), 3.88 (d, J=7.30 Hz, 1H), 4.35 (d, J=6.90 Hz, 1H), 4.42 (, d, J=7.03 Hz, 1H), 5.18-5.25 (m, 2H), 6.67 (s, 1H), 7.10-7.15 (m, 2H), 7/17-7.20 (m, 1H), 7.55 (s, 1H).

Example 7

Intermediate 10

2-(2-tert-Butoxycarbonylamino-3-methyl-butyrylamino)-3-methyl-butyric acid 3-[(S)-1-(1H-imidazol-4-yl)-ethyl]-2-methyl-benzyl ester The title compound was prepared from Intermediate 9 (750 mg, 1.05 mmol) in 30 ml of MeOH according to the procedure described in Example 2.

$^1$H-NMR ($CD_3OD$; δ ppm): 0.89 (d, d, J=7.03 Hz, 6H), 1.44 (s, 9H), 1.54 (d, J=7.33 Hz, 3H), 2.14 (hept, J=6.74 Hz, 1H), 2.33 (s, 3H), 3.74 (s, 2H), 4.35-4.55 (m, 2H), 5.20 (s, 2H), 6.67 (s, 1H), 7.10-7.17 (m, 2H), 7.19-7.23 (m, 1H), 7.56 (s, 1H).

Example 8

Compound 8

2-(2-Amino-3-methyl-butyrylamino)-3-methyl-butyric acid 3-[(S)-1-(1H-imidazol-4-yl)-ethyl]-2-methyl-benzyl ester

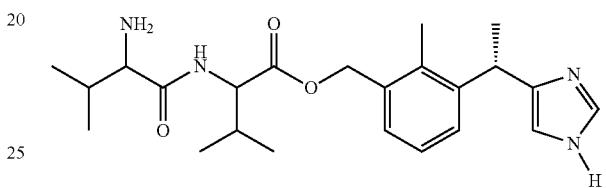

The title compound was prepared from Intermediate 10 (450 mg, 0.87 mmol) in 8 ml of 4N HCl/Dioxane according to the procedure described in Example 5.

$^1$H-NMR ($CD_3OD$; δ ppm): 0.85 (d, J=7.03 Hz, 3H), 0.91 (d, J=6.74 Hz, 3H), 0.92 (d, J=7.3 Hz. 3H), 1.14 (d, J=6.2 Hz, 3H), 1.54 (d, J=7.03 Hz, 3H), 1.94 (hept, J=5.2 Hz, 1H), 2.14 (hept, J=6.2 Hz, 1H), 2.33 (s, 3H), 3.18 (d, J=5.2 Hz, 1H), 4.34 (d, J=6.2 Hz, 1H), 4.42 (q, J=7.03 Hz, 1H), 5.21-5.26 (m, 2H), 6.67 (s, 1H), 7.10-7.15 (m, 2H), 7.18-7.20 (m, 1H), 7.55 (s, 1H).

Example 9

Intermediate 11

2-(2-tert-Butoxycarbonylamino-acetylamino)-3-methyl-butyric acid 3-[(S)-1-(1H-imidazol-4-yl)-ethyl]-2-methyl-benzyl ester The title compound was prepared from Compound 8 (405 mg, 1.28 mmol), Boc-Glycine (675 mg, 3.86 mmol), EDCI (859 mg, 4.48 mmol) and DMAP (547 mg, 4.48 mmol) according to the procedure described in Example 3. The title compound was purified by column chromatography using 5% 7N $NH_3$/MeOH in DCM.

$^1$H-NMR ($CD_3OD$; δ ppm): 0.89 (d, J=6.74 Hz, 3H), 0.91 (d, J=6.74 Hz, 3H), 1.55 (d, J=7.30 Hz, 3H), 2.14 (hept, J=6.74 Hz, 1H), 2.33 (s, 3H), 4.37 (d, J=5.90 Hz, 1H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

Example 10

Compound 9

2-(2-Amino-acetylamino)-3-methyl-butyric acid 3-[(S)-1-(1H-imidazol-4-yl)-ethyl]-2-methyl-benzyl ester

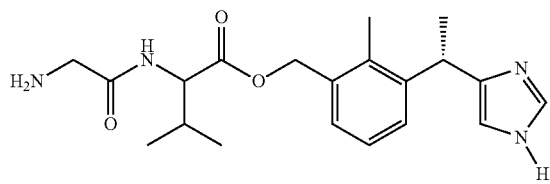 [SMILES: Cc1c(COC(=O)C(NC(=O)CN)C(C)C)cccc1[C@H](C)c1c[nH]cn1]

The title compound was prepared from Intermediate 11 (320 mg, 0.68 mmol) with 10 ml of 4N HCl/Dioxane according the procedure described in Example 5.

$^1$H-NMR (CD$_3$OD; δ ppm): 0.89 (d, J=6.74 Hz, 3H), 0.91 (d, J=6.74 Hz, 3H), 2.14 (hept, J=6.74 Hz, 1H), 2.33 (s, 3H), 4.37 (d, J=5.90 Hz, 1H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

Example 11

Intermediate 12

2-tert-Butoxycarbonylamino-3-phenyl-propionic acid 3-[(S)-1-(1H-imidazol-4-yl)-ethyl]-2-methyl-benzyl ester The title compound was prepared from (S)-[3-(1-(1H-imidazol-4-yl)ethyl)-2-methylphenyl]methanol (216 mg, 1.0 mmol), Boc-L-Phenylalanine (795 mg, 3.0 mmol), EDCI (671 mg, 3.5 mmol) and DMAP (427 mg, 3.5 mmol) according to the procedure described in Example 3. Intermediate 12 was purified by a column chromatography using 35-100% ethyl acetate in hexane.

$^1$H-NMR (CD$_3$OD; δ ppm): 1.36 (s, 9H), 1.55 (d, J=7.03 Hz, 3H), 2.28 (s, 3H), 2.85-2.95 (m, 1H), 3.05-3.11 (m, 1H), 4.38 (m, 1H), 4.40 (q, J=7.03 Hz, 1H), 5.17 (s, 2H), 6.69 (s, 1H), 7.08-7.24 (m, 8H), 7.55 (s, 1H).

Example 12

Compound 10

2-Amino-3-phenyl-propionic acid 3-[(S)-1-(1H-imidazol-4-yl)-ethyl]-2-methyl-benzyl ester

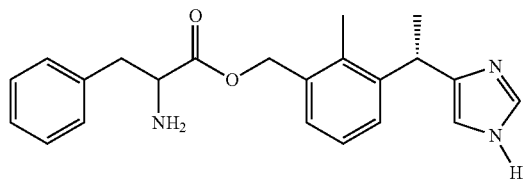 [SMILES: Cc1c(COC(=O)C(N)Cc2ccccc2)cccc1[C@H](C)c1c[nH]cn1]

The title compound was prepared from Intermediate 12 (240 mg, 0.52 mmol) with 8 ml of 4N HCl/Dioxane according to the procedure described in Example 5.

$^1$H-NMR (CD$_3$OD; δ ppm): 1.54 (d, J=7.03 Hz, 3H), 2.26 (s, 3H), 2.90-3.00 (m, 2H), 3.73 (t, J=6.40 Hz, 1H), 4.40 (q, J=7.03 Hz, 1H), 5.13-5.18 (m, 2H), 6.68 (s, 1H), 7.08-7.12 (m, 5H), 7.13-7.22 (m, 3H), 7.55 (s, 1H).

The following assay was used to demonstrate the potency and selectivity of the compounds according to the invention.

Example 13

The experimental animals used, were Normotensive male Dutch-Belted rabbits (Myrtle's Rabbitry) over 6 months in age (n=4/compound/dose screened). A single drop (50 μl) of the drug formulation, which yields 0.15% or 0.3% of the active metabolite when completely hydrolyzed in 1% polysorbate 80 at pH 5.5, was administered topically by pipette onto the right eye (treated eye) at approximately 0700 hours. IOP of the rabbits (treated and untreated eyes) was measured 0 hours before and at 0.5, 1, 2, 3, 4, 6 and 8 hours after topical eyedrop administration. IOP at the time of eye drop administration (0 hours) was used as a baseline value. Prior to the tonometric measurements, 0.05% proparacaine (50 μl) was administered to each eye. Tonometric IOP measurements were obtained with a Mentor Pneumontonmeter. Additionally, all studies were masked. At least 1 week of wash-out time was allowed for each rabbit between dosings. All animals were examined for sedation, ocular irritation, and changes in pupil diameter throughout the course of the experiments.

The data collected from the compounds of the present invention, IOP experiments, showed that the pro-drug iso-Butyric acid 3-[(S)-1-(1H-imidazol-4-yl)-ethyl]-2-methyl-benzyl ester has an IOP lowering capacity at the tested concentration that has equal or comparable efficacy to Alphagan P® and has longer intraocular pressure duration than Alphagan P®(FIG. 1).

Example 14

This example shows the intraocular pressure-lowering effect of iso-Butyric acid 3-[(S)-1-(1H-imidazol-4-yl)-ethyl]-2-methyl-benzyl ester containing composition as compared to placebo. The intraocular pressure of the monkeys treated with the iso-Butyric acid 3-[(S)-1-(1H-imidazol-4-yl)-ethyl]-2-methyl-benzyl ester containing composition, maintain the decrease in intraocular pressure for up to 24 hours.

What is claimed is:

1. A method of lowering intraocular pressure in a subject in need of such treatment, which comprises administering a therapeutically effective amount of a composition comprising a compound having Formula I, its individual enantiomers, its individual tautomers or a pharmaceutically acceptable salt thereof,

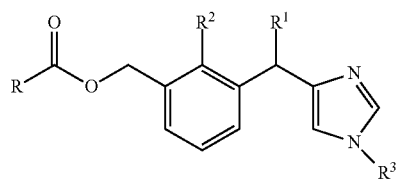

Formula I wherein
R$^1$ is H or C$_{1-3}$ alkyl;
R$^2$ is H or C$_{1-3}$ alkyl;

R³ is H, C$_{1-10}$ alkyl, heterocycle or aryl; and
R is C$_{1-10}$ alkyl, heterocycle or aryl.

2. A method according to claim 1, wherein the compound is of Formula II, its individual tautomers or a pharmaceutically acceptable salt thereof,

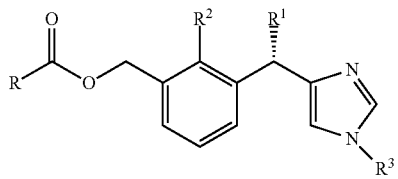

Formula II wherein
R¹ is H or C$_{1-3}$ alkyl;
R² is H or C$_{1-3}$ alkyl;
R³ is H, C$_{1-10}$ alkyl, heterocycle or aryl; and
R is C$_{1-10}$ alkyl, heterocycle or aryl.

3. A method according to claim 1, wherein the compound is of Formula III, its individual tautomers or a pharmaceutically acceptable salt thereof,

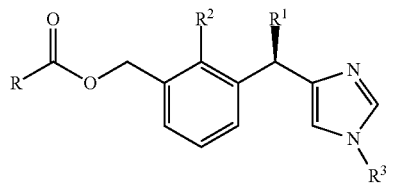

Formula III wherein
R¹ is H or C$_{1-3}$ alkyl;
R² is H or C$_{1-3}$ alkyl;
R³ is H, C$_{1-10}$ alkyl, heterocycle or aryl; and
R is C$_{1-10}$ alkyl, heterocycle or aryl.

4. A method according to claim 2, wherein R¹ is C$_{1-3}$ alkyl, R² is C$_{1-3}$ alkyl, R³ is H and R is C$_{1-10}$ alkyl.

5. A method according to claim 2, wherein R¹ is methyl, R² is methyl, R³ is H and R is C$_{1-4}$ alkyl.

6. A method according to claim 2, wherein the compound is selected from:
iso-Butyric acid 3-[(S)-1-(1H-imidazol-4-yl)ethyl]-2-methyl-benzyl ester;
2,2-Dimethyl-propionic acid 3-[(S)-1-(1H-imidazol-4-yl)ethyl]-2-methyl-benzyl ester;
Acetic acid 3-[(S)-1-(1H-imidazol-4-yl)ethyl]-2-methyl-benzyl ester;
Benzoic acid 3-[(S)-1-(1H-imidazol-4-yl)-ethyl]-2-methyl-benzyl ester;
3-Methyl-butyric acid 3-[(S)-1-(1H-imidazol-4-yl)-ethyl]-2-methyl-benzyl ester;
3-Phenyl-propionic acid 3-[(S)-1-(1H-imidazol-4-yl)-ethyl]-2-methyl-benzyl ester;
2-Amino-3-methyl-butyric acid 3-[(S)-1-(1H-imidazol-4-yl)-ethyl]-2-methyl-benzyl ester;
2-(2-Amino-3-methyl-butyrylamino)-3-methyl-butyric acid 3-[(S)-1-(1H-imidazol-4-yl)-ethyl]-2-methyl-benzyl ester;
2-(2-Amino-acetylamino)-3-methyl-butyric acid 3-[(S)-1-(1H-imidazol-4-yl)-ethyl]-2-methyl-benzyl ester; and
2-Amino-3-phenyl-propionic acid 3-[(S)-1-(1H-imidazol-4-yl)ethyl]-2-methyl-benzyl ester.

7. A method according to claim 2, wherein the compound is selected from
iso-Butyric acid 3-[(S)-1-(1-iso-butyryl-1H-imidazol-4-yl)-ethyl]-2-methyl-benzyl ester;
2,2-Dimethyl-propionic acid 3-{(S)-1-[1-(2,2-dimethyl-propionyl)-1H-imidazol-4-yl]-ethyl}-2-methyl-benzyl ester;
Acetic acid 3-[(S)-1-(1-acetyl-1H-imidazol-4-yl)-ethyl]-2-methyl-benzyl ester;
Benzoic acid 3-[(S)-1-(1-benzoyl-1H-imidazol-4-yl)-ethyl]-2-methyl-benzyl ester;
3-Methyl-butyric acid 2-methyl-3-{(S)-1-[1-(3-methyl-butyryl)-1H-imidazol-4-yl]-ethyl}-benzyl ester;
Phenyl-propionic acid 2-methyl-3-{(S)-1-[1-(3-phenyl-propionyl)-1H-imidazol-4-yl]-ethyl}-benzyl ester;
2-tert-Butoxycarbonylamino-3-methyl-butyric acid 3-{(S)-1-[1-(2-tert-butoxy carbonylamino-3-methyl-butyryl)-1H-imidazol-4-yl]-ethyl}-2-methyl-benzyl ester;
2-tert-Butoxycarbonylamino-3-methyl-butyric acid 3-[(S)-1-(1H-imidazol-4-yl)-ethyl]-2-methyl-benzyl ester;
2-(2-tert-Butoxycarbonylamino-3-methyl-butyrylamino)-3-methyl-butyric acid 3-{(S)-1-[1-(2-tert-butoxycarbonylamino-3-methyl-butyryl)-1H-imidazol-4-yl]-ethyl}-2-methyl-benzyl ester;
2-(2-tert-Butoxycarbonylamino-3-methyl-butyrylamino)-3-methyl-butyric acid 3-[(S)-1-(1H-imidazol-4-yl)-ethyl]-2-methyl-benzyl ester;
2-(2-tert-Butoxycarbonylamino-acetylamino)-3-methyl-butyric acid 3-[(S)-1-(1H-imidazol-4-yl)-ethyl]-2-methyl-benzyl ester; and
2-tert-Butoxycarbonylamino-3-phenyl-propionic acid 3-[(S)-1-(1H-imidazol-4-yl)-ethyl]-2-methyl-benzyl ester.

8. The method of claim 1, wherein the affected eye maintains an intraocular pressure less than the baseline intraocular pressure for at least eight (8) hours.

9. The method of claim 1, wherein the affected eye maintains an intraocular pressure less than the baseline intraocular pressure for at least ten (10) hours.

10. The method of claim 1, wherein the affected eye maintains an intraocular pressure less than the baseline intraocular pressure for at least twelve (12) hours.

11. The method of claim 1, wherein the composition comprises 0.0005% to 5% by weight, of a compound selected from:
iso-Butyric acid 3-[(S)-1-(1H-imidazol-4-yl)ethyl]-2-methyl-benzyl ester;
2,2-Dimethyl-propionic acid 3-[(S)-1-(1H-imidazol-4-yl)ethyl]-2-methyl-benzyl ester;
Acetic acid 3-[(S)-1-(1H-imidazol-4-yl)ethyl]-2-methyl-benzyl ester;
Benzoic acid 3-[(S)-1-(1H-imidazol-4-yl)-ethyl]-2-methyl-benzyl ester;
3-Methyl-butyric acid 3-[(S)-1-(1H-imidazol-4-yl)-ethyl]-2-methyl-benzyl ester;
3-Phenyl-propionic acid 3-[(S)-1-(1H-imidazol-4-yl)-ethyl]-2-methyl-benzyl ester;
2-Amino-3-methyl-butyric acid 3-[(S)-1-(1H-imidazol-4-yl)-ethyl]-2-methyl-benzyl ester;
2-(2-Amino-3-methyl-butyrylamino)-3-methyl-butyric acid 3-[(S)-1-(1H-imidazol-4-yl)-ethyl]-2-methyl-benzyl ester;
2-(2-Amino-acetylamino)-3-methyl-butyric acid 3-[(S)-1-(1H-imidazol-4-yl)-ethyl]-2-methyl-benzyl ester; and
2-Amino-3-phenyl-propionic acid 3-[(S)-1-(1H-imidazol-4-yl)ethyl]-2-methyl-benzyl ester;

or a pharmaceutically acceptable salt thereof.

12. The method of claim 1, wherein the composition comprises 0.005% to 2% by weight, of a compound selected from:
- iso-Butyric acid 3-[(S)-1-(1H-imidazol-4-yl)ethyl]-2-methyl-benzyl ester;
- 2,2-Dimethyl-propionic acid 3-[(S)-1-(1H-imidazol-4-yl)ethyl]-2-methyl-benzyl ester;
- Acetic acid 3-[(S)-1-(1H-imidazol-4-yl)ethyl]-2-methyl-benzyl ester;
- Benzoic acid 3-[(S)-1-(1H-imidazol-4-yl)-ethyl]-2-methyl-benzyl ester;
- 3-Methyl-butyric acid 3-[(S)-1-(1H-imidazol-4-yl)-ethyl]-2-methyl-benzyl ester;
- 3-Phenyl-propionic acid 3-[(S)-1-(1H-imidazol-4-yl)-ethyl]-2-methyl-benzyl ester;
- 2-Amino-3-methyl-butyric acid 3-[(S)-1-(1H-imidazol-4-yl)-ethyl]-2-methyl-benzyl ester;
- 2-(2-Amino-3-methyl-butyrylamino)-3-methyl-butyric acid 3-[(S)-1-(1H-imidazol-4-yl)-ethyl]-2-methyl-benzyl ester;
- 2-(2-Amino-acetylamino)-3-methyl-butyric acid 3-[(S)-1-(1H-imidazol-4-yl)-ethyl]-2-methyl-benzyl ester; and
- 2-Amino-3-phenyl-propionic acid 3-[(S)-1-(1H-imidazol-4-yl)ethyl]-2-methyl-benzyl ester;

or a pharmaceutically acceptable salt thereof.

13. The method of claim 1, wherein the composition comprises 0.05% to 2% by weight, of a compound selected from:
- iso-Butyric acid 3-[(S)-1-(1H-imidazol-4-yl)ethyl]-2-methyl-benzyl ester;
- 2,2-Dimethyl-propionic acid 3-[(S)-1-(1H-imidazol-4-yl)ethyl]-2-methyl-benzyl ester;
- Acetic acid 3-[(S)-1-(1H-imidazol-4-yl)ethyl]-2-methyl-benzyl ester;
- Benzoic acid 3-[(S)-1-(1H-imidazol-4-yl)-ethyl]-2-methyl-benzyl ester;
- 3-Methyl-butyric acid 3-[(S)-1-(1H-imidazol-4-yl)-ethyl]-2-methyl-benzyl ester;
- 3-Phenyl-propionic acid 3-[(S)-1-(1H-imidazol-4-yl)-ethyl]-2-methyl-benzyl ester;
- 2-Amino-3-methyl-butyric acid 3-[(S)-1-(1H-imidazol-4-yl)-ethyl]-2-methyl-benzyl ester;
- 2-(2-Amino-3-methyl-butyrylamino)-3-methyl-butyric acid 3-[(S)-1-(1H-imidazol-4-yl)-ethyl]-2-methyl-benzyl ester;
- 2-(2-Amino-acetylamino)-3-methyl-butyric acid 3-[(S)-1-(1H-imidazol-4-yl)-ethyl]-2-methyl-benzyl ester; and
- 2-Amino-3-phenyl-propionic acid 3-[(S)-1-(1H-imidazol-4-yl)ethyl]-2-methyl-benzyl ester;

or a pharmaceutically acceptable salt thereof.

14. The method of claim 1, wherein the composition further comprises from 0.001% to 1% by weight of a preservative.

15. The method of claim 1, wherein the composition further comprises from 0.01% to 0.5% by weight of a preservative.

16. The method of claim 1, wherein the composition further comprises from 0.001% to 0.01% by weight of a preservative.

17. The method of claim 1, wherein the composition further comprises from 0.01% to 1% by weight of a co-solvent.

18. The method of claim 1, wherein tthe composition further comprises from 0.01% to 2% by weight of a viscosity building agent.

\* \* \* \* \*

UNITED STATES PATENT AND TRADEMARK OFFICE
CERTIFICATE OF CORRECTION

PATENT NO. : 8,501,796 B2
APPLICATION NO. : 13/233844
DATED : August 6, 2013
INVENTOR(S) : Mohammad I. Dibas et al.

It is certified that error appears in the above-identified patent and that said Letters Patent is hereby corrected as shown below:

On Title page 2, in column 2, under "Other Publications", line 13, delete "Chemica" and insert -- Chimica --, therefor.

In the Specification

In column 1, line 43, delete "Y.-H" and insert -- Y. H --, therefor.

In column 1, line 21, delete "methanolor" and insert -- methanol or --, therefor.

In column 2, line 48, after "enantiomers" insert -- . --.

In column 4, line 15, delete "orchiectomyatopic" and insert -- orchiectomy atopic --, therefor.

In column 4, line 19, delete "rhinophymia" and insert -- rhinophyma --, therefor.

In column 4, line 23, delete "cutenous" and insert -- cutaneous --, therefor.

In column 6, line 46, delete "trialklysilyl" and insert -- trialkylsilyl --, therefor.

In column 8, line 22, delete "—O(" and insert -- —C( --, therefor.

In column 8, line 23, delete "$C_{1-6}$alkyl" and insert -- $C_{1-6}$ alkyl --, therefor.

In column 8, line 29, delete "isooxazolyl" and insert -- isoxazolyl --, therefor.

In column 8, line 39, delete "naphtyl." and insert -- naphthyl. --, therefor.

In column 8, line 41, delete "—O(" and insert -- —C( --, therefor.

In column 8, line 43, delete "naphtyl." and insert -- naphthyl. --, therefor.

In column 8, line 51, delete "—O(" and insert -- —C( --, therefor.

In column 9, line 20, delete "yl)ethyl" and insert -- yl)-ethyl --, therefor.

In column 9, lines 22-23, delete "yl)ethyl" and insert -- yl)-ethyl --, therefor.

In column 9, line 24, delete "yl)ethyl" and insert -- yl)-ethyl --, therefor.

In column 10, line 37, delete "palmoic" and insert -- pamoic --, therefor.

In column 10, line 37, delete "palmoic" and insert -- pamoic --, therefor.

Signed and Sealed this
Twenty-sixth Day of November, 2013

Margaret A. Focarino
*Commissioner for Patents of the United States Patent and Trademark Office*

CERTIFICATE OF CORRECTION (continued)
U.S. Pat. No. 8,501,796 B2

In column 10, lines 37-38, delete "naphthalene-sulfonic" and insert -- naphthalenesulfonic --, therefor.

In column 10, line 38, delete "napthalenedisulfonic" and insert -- naphthalenedisulfonic --, therefor.

In column 10, line 42, delete "Stahal" and insert -- Stahl --, therefor.

In column 10, line 43, delete "Chemica" and insert -- Chimica --, therefor.

In column 10, line 53, delete "cinnamoate" and insert -- cinnamate --, therefor.

In column 10, line 53, delete "mandeloate" and insert -- mandelate --, therefor.

In column 10, line 53, delete "benzyloate" and insert -- benzoate --, therefor.

In column 12, line 1, delete "the a" and insert -- the --, therefor.

In column 13, line 49, delete "bodium" and insert -- sodium --, therefor.

In column 15, line 36, delete "tertahydrofuran" and insert -- tetrahydrofuran --, therefor.

In column 16, line 35, delete "tertahydrofuran" and insert -- tetrahydrofuran --, therefor.

In column 16, line 42, delete "EDCl" and insert -- EDCl --, therefor.

In column 17, line 40 (Table 1), delete "yl]ethyl" and insert -- yl]-ethyl --, therefor.

In column 18, line 10 (Table-continued 1), delete "yl]ethyl" and insert -- yl]-ethyl --, therefor.

In column 21, line 45, delete "EDCl" and insert -- EDCl --, therefor.

In column 21, line 50, delete "Hz," and insert -- Hz, 3H), --, therefor.

In column 24, line 19, delete "eyedrop" and insert -- eye drop --, therefor.

In column 24, line 23, delete "Pneumontonmeter." and insert -- Pneumotonometer. --, therefor.

In the Claims

In column 25, line 47, in claim 6, delete "yl)ethyl" and insert -- yl)-ethyl --, therefor.

In column 25, lines 49-50, in claim 6, delete "yl)ethyl" and insert -- yl)-ethyl --, therefor.

In column 25, line 51, in claim 6, delete "yl)ethyl" and insert -- yl)-ethyl --, therefor.

In column 25, line 67, in claim 6, delete "yl)ethyl" and insert -- yl)-ethyl --, therefor.

In column 26, line 2, in claim 7, delete "from" and insert -- from: --, therefor.

In column 26, line 17, in claim 7, delete "butoxy carbonylamino" and insert -- butoxycarbonylamino --, therefor.

In column 26, line 47, in claim 11, delete "yl)ethyl" and insert -- yl)-ethyl --, therefor.

In column 26, lines 49-50, in claim 11, delete "yl)ethyl" and insert -- yl)-ethyl --, therefor.

In column 26, line 51, in claim 11, delete "yl)ethyl" and insert -- yl)-ethyl --, therefor.

In column 26, line 67, in claim 11, delete "yl)ethyl" and insert -- yl)-ethyl --, therefor.

In column 27, line 4, in claim 12, delete "yl)ethyl" and insert -- yl)-ethyl --, therefor.

In column 27, lines 6-7, in claim 12, delete "yl)ethyl" and insert -- yl)-ethyl --, therefor.

In column 27, line 8, in claim 12, delete "yl)ethyl" and insert -- yl)-ethyl --, therefor.

CERTIFICATE OF CORRECTION (continued)
U.S. Pat. No. 8,501,796 B2

In column 27, line 24, in claim 12, delete "yl)ethyl" and insert -- yl)-ethyl --, therefor.

In column 27, line 28, in claim 13, delete "yl)ethyl" and insert -- yl)-ethyl --, therefor.

In column 27, line 30, in claim 13, delete "yl)ethyl" and insert -- yl)-ethyl --, therefor.

In column 27, line 32, in claim 13, delete "yl)ethyl" and insert -- yl)-ethyl --, therefor.

In column 28, line 15, in claim 13, delete "yl)ethyl" and insert -- yl)-ethyl --, therefor.

In column 28, line 30, in claim 18, delete "tthe" and insert -- the --, therefor.